United States Patent
McNair

(10) Patent No.: US 10,916,345 B1
(45) Date of Patent: *Feb. 9, 2021

(54) ASSESSING FITNESS BY ENTROPY AND BISPECTRAL ANALYSIS

(71) Applicant: CERNER INNOVATION, INC., Kansas City, KS (US)

(72) Inventor: Douglas S. McNair, Leawood, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 341 days.

This patent is subject to a terminal disclaimer.

(21) Appl. No.: 15/888,955

(22) Filed: Feb. 5, 2018

Related U.S. Application Data

(63) Continuation of application No. 13/775,562, filed on Feb. 25, 2013, now Pat. No. 9,886,559.

(60) Provisional application No. 61/603,178, filed on Feb. 24, 2012.

(51) Int. Cl.
  *G16H 50/20* (2018.01)
  *G16H 20/30* (2018.01)

(52) U.S. Cl.
  CPC ............. *G16H 50/20* (2018.01); *G16H 20/30* (2018.01)

(58) Field of Classification Search
  CPC .......... G16G 50/20; G13H 20/30; A61B 5/11; A61B 5/112; A61B 5/1118; A61B 5/1121; A61B 5/1124
  See application file for complete search history.

(56) References Cited

U.S. PATENT DOCUMENTS

| | | | |
|---|---|---|---|
| 4,195,643 A | 4/1980 | Pratt, Jr. | |
| 5,029,483 A | 7/1991 | Gautschi et al. | |
| 5,365,787 A | 11/1994 | Hernandez et al. | |
| 5,913,242 A | 6/1999 | Stussi | |
| 7,363,172 B2 | 4/2008 | Nichols et al. | |
| 7,402,142 B2 | 7/2008 | Kawai et al. | |
| 2005/0240086 A1* | 10/2005 | Akay | A61B 5/0002 600/300 |
| 2008/0045804 A1 | 2/2008 | Williams | |
| 2009/0069722 A1 | 3/2009 | Flaction et al. | |
| 2010/0169030 A1 | 7/2010 | Parlos | |

(Continued)

*Primary Examiner* — Patrick Fernandes
(74) *Attorney, Agent, or Firm* — Shook, Hardy and Bacon, L.L.P.

(57) ABSTRACT

Methods, systems, and computer-readable media are provided for enabling improvements in athlete training and injury management through entropy and third-order spectral analysis of digitized force-vs-time time series from movements. In embodiments, entropy and/or bispectral statistics are determined using time-series information obtained from movements of an athlete, such as squat jump and countermovement jump maneuvers, using a biomechanical sensor, such as a digital force plate apparatus. These statistics may be used to facilitate sports medicine and health management of the athlete. In some embodiments, where athletes are involved in sport that involves explosive power development in the lower extremities and extensive running, cutting, jumping or other movement having risk of injuries to the lower extremities, time series force plate data are obtained and transformed to calculate entropy and bispectral statistics, from which functional status of the lower limbs and readiness for safe return-to-play may be ascertained.

20 Claims, 12 Drawing Sheets

(56) References Cited

U.S. PATENT DOCUMENTS

| | | |
|---|---|---|
| 2010/0317489 A1 | 12/2010 | Flaction |
| 2011/0052005 A1 | 3/2011 | Selner |
| 2011/0054359 A1 | 3/2011 | Sazonov et al. |
| 2012/0010535 A1 | 1/2012 | Kubiak et al. |

\* cited by examiner

ASSESSING FITNESS BY ENTROPY AND BISPECTRAL ANALYSIS

CROSS-REFERENCE TO RELATED APPLICATIONS

This application is a continuation application of U.S. patent application Ser. No. 13/775,562, titled "Assessing Fitness By Entropy And Bispectral Analysis," filed on Feb. 25, 2013, which claims the benefit of U.S. Provisional Application No. 61/603,178, titled "Assessing Fitness By Entropy And Bispectral Analysis," filed Feb. 24, 2012, both of which are hereby expressly incorporated herein by reference in their entireties.

INTRODUCTION

Injuries to the lower extremity (ankle, knee, hip, foot, muscle and soft tissues of the leg, etc.) are among the most common injuries suffered in today's athletic population, and these injuries are most prevalent in cutting and jumping sports such as basketball, soccer, football, and volleyball. For example, in the past thirty years the game of basketball has evolved from a game of finesse to its current categorization as a high-impact contact sport. Modern basketball emphasizes the speed and power of the competitors. For example, athletes in the NBA, in particular, play on a longer court, accumulate more minutes-played, play more times per week and for a longer season, and are older than collegiate players. With reference to the table below, the frequency and intensity of play expose NBA athletes to a high risk of injury over their 9-month season. More than half of all game-related injuries involve the lower extremity.

| Anatomical Structure | Game injuries (1988-1998) | Pct of all game injuries | Rate (per 10K min-played) | Rate (per 1K AEs) |
| --- | --- | --- | --- | --- |
| Ankle | 724 | 16.9 | 1.5 | 3.6 |
| Femur | 337 | 7.9 | 0.7 | 1.7 |
| Knee | 308 | 7.2 | 0.6 | 1.5 |
| Lumbar spine | 271 | 6.3 | 0.6 | 1.4 |
| Tibia | 239 | 5.6 | 0.5 | 1.2 |
| Patellofemoral | 236 | 5.5 | 0.5 | 1.2 |
| Shoulder | 184 | 4.3 | 0.4 | 0.9 |
| Foot | 181 | 4.2 | 0.4 | 0.9 |
| Hip | 164 | 3.8 | 0.3 | 0.8 |
| Wrist | 133 | 3.1 | 0.3 | 0.7 |
| Hand | 130 | 3.0 | 0.3 | 0.7 |
| Fingers | 123 | 2.9 | 0.3 | 0.6 |
| Toes | 80 | 1.9 | 0.2 | 0.4 |

For example, it has been reported that the injury recurrence rate after a lateral ankle sprain is as high as 80%. This is a significant concern for athletes and for athletic trainers, physical therapists, and team owners and managers, because athletes bear far higher risk of long-term disability and degeneration after an initial traumatic episode. Furthermore, athletes who experience more ankle sprains present with residual symptoms that are more severe than those less frequently injured do, with pain typically reported as the most common residual symptom, and a subject's reported sense of joint or limb instability rated as the second most common residual symptom. It should be noted, however, that there are a number of residual abnormalities that are experienced during the recovery period following an injury that are difficult for an athlete to describe orally, and therefore are seldom reported as symptoms and thus underrepresented.

Although speculations have been made regarding the cause of long-term pain, dysfunction, and disability associated with injuries to the lower extremity and referred to as chronic instability, the exact reason for these problems remains unclear. The source of the chronic joint and limb dysfunction has traditionally been described as an either mechanical or functional instability. For example, the term 'functional joint instability' describes the subjective feeling of "giving way" of the foot and ankle or "uncertainty as to the joint's ability to accept weight". Other definitions characterize the condition as a "history of joint insecurity", and there is presently a refinement of the criteria used to classify individuals as 'functionally' unstable.

Conversely, 'mechanical' instability involves structural damage to the support network (muscles, ligaments, tendons, proprioception and other neurological components, vascular components) surrounding the joint complex and is sometimes termed 'ligamentous laxity' or 'hypermobility'. In one sense, the relationship between mechanical instability and functional instability may be considered not as mutually exclusive entities, but as a 'continuum' of pathologic contributions to chronic instability." The subtleties and ambiguities of such a continuum pose assessment difficulties for trainers, therapists, and physicians. Subjective self-reporting of symptoms by the athlete is imprecise, and qualitative physical examination and diagnostic imaging methods are too insensitive to detect substantial abnormalities that are present.

Attempts to address these problems encounter challenges and limitations, including:

(1) Inaccuracy and imprecision with regard to classifying the athlete as fit for play or unfit to resume play, including both excessive false-negative rate (e.g., missed diagnoses; under-estimation of residual disability from prior injury; premature decision to permit return-to-play (RTP)) and excessive false-positive rate (e.g., over-estimation of disability; prolonged restriction from RTP). Many of these errors arise from both procedural and technical causes such as, for example: (a) Certain measurement methods (e.g., range-of-motion, strength, joint flexibility, palpation, etc.) which have inherently large imprecision (high within-individual variability as well as high inter-observer variability; high coefficient of variation CV %) and large deviations in scale and bias (low intra-class correlation ICC). (b) Incomplete assessments, such as assessments that are established based on exam procedures involving one or only a few repetitions of movements. Under-sampling exacerbates the said inaccuracy and imprecision of the measurement methods. (c) Assessments that are not made under conditions that physically emulate actual sporting play in terms of kinetic and kinematic load magnitudes and volumes.

(2) Reliance on only 'peak' values such as measurements of strength or speed or jump height or range of motion, neglecting detailed 'mid-course' temporal information from single performances of a movement and neglecting time trend information from multiple, serial performances of movements that elicit neuromuscular recruitment and fatigue during the course of the repetitions.

(3) Reliance on self-reported symptoms verbalized by the athlete. Symptoms are frequently under-reported by the athlete, who typically is under strong incentive or pressure for excessively early RTP or "playing through the pain". Symptoms are also frequently under-diagnosed by trainers and medical personnel, who sometimes experience ambiguous or conflicting pressures from team owners or management.

Accordingly, it is therefore desirable to establish systems and methods for deriving more accurate and reliable diagnostic, monitoring, and predictive measures of athletic movement, such as lower extremity function, that take advantage of detailed time-oriented information available from a biomechanical sensor, such as a force plate digitization apparatus.

SUMMARY

A system, methods and computer-readable media are provided for facilitating patient injury management, and for enabling improvements in athlete training through entropy and third-order spectral analysis of digitized force-vs-time time series from movements. In embodiments, entropy and/or bispectral statistics are determined using time-series information obtained from movements of an athlete using a biomechanical sensor. In some embodiments, such as where athletes are involved in sport that involves explosive power development in the lower extremities and extensive running, cutting, jumping or other movement having risk of injuries to the lower extremities, time series force plate data are obtained and transformed to calculate entropy and bispectral statistics, from which functional status of the lower limbs and readiness for safe return-to-play may be ascertained. In this way, embodiments of the invention may be used to quantitatively measure baseline performance of the lower extremity in explosive "jump" movements that impose large forces and moments on the structures of the lower limbs. Further, embodiments of the invention may be used to enable sensitive and specific detection of residual abnormalities that are subtle and difficult to describe or report as symptoms and yet are critical to safe and accurate certification of an athlete for return-to-play (RIP) after injury, thereby preventing a percentage of recurrent injuries and long-term disability. Still further, embodiments of the invention may be used to facilitate the monitoring of the recovery process and activity prescription that will be safely tolerated during recovery.

BRIEF DESCRIPTION OF THE DRAWINGS

Embodiments of the invention are described in detail below with reference to the attached drawing figures, wherein.

DETAILED DESCRIPTION

Figure 1A:
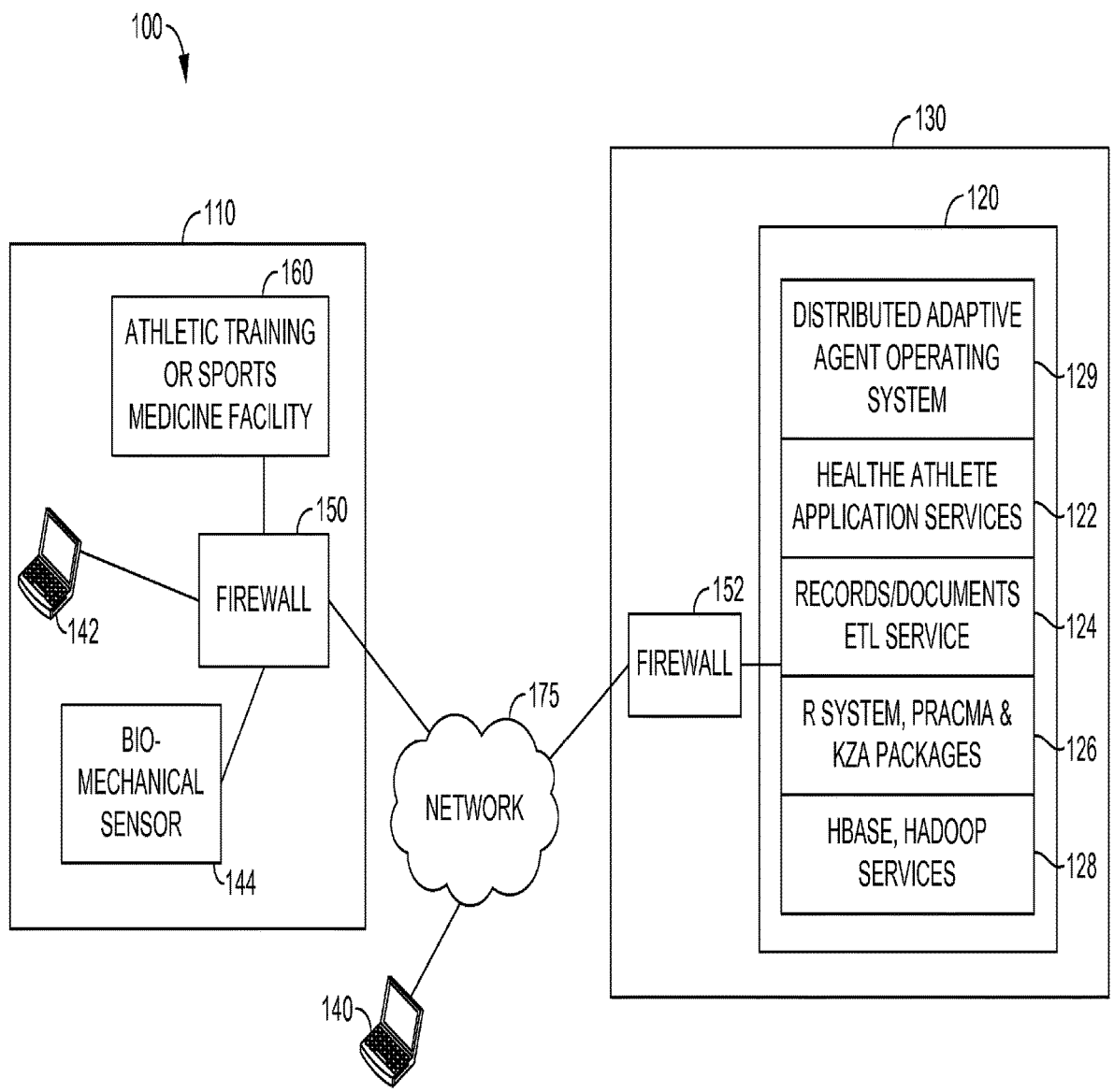
FIGS. 1A, 1B, and 1C depict aspects of an illustrative operating environment suitable for practicing embodiments of the invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and nonvolatile media, removable nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other storage devices. These technologies can store data momentarily, temporarily, or permanently.

Embodiments of this technology are provided for facilitating injury management of patients including management of athletes who are involved in sport that involves explosive power development in the lower extremities and extensive running, cutting, and jumping. In particular, embodiments apply approximate entropy (ApEn) and bispectra to the examination and assessment of kinetic and kinematic functioning of the human machine, specifically the elements that comprise the lower extremity, in some embodiments. In some embodiments there is provided a measurement method and a measurement device enabling the lower-extremity fitness and movement capacity of athletes to be evaluated. In some embodiments, time series information acquired via a digital force plate or other biomechanical sensor are transformed to calculate entropy and bispectral statistics, from which functional status of the limbs and readiness for safe return-to-play may be ascertained. In some embodiments, a sports performance measurement method and apparatus is provided specifically intended for training and for rehabilitation of the lower extremity, involving for example known muscular tests such as jumping maneuvers. In particular, some embodiments may be used for enabling force, velocity, and power development of athletes to be measured by means of brief testing involving a series of repetitions of squat jumps or countermovement jumps under conditions that accurately reflect loads and intensities that characterize sporting competition. In this way, embodiments provide a rapid test with an instrument which is simple to use, is noninvasive, and is capable of immediately delivering data representative of lower extremity-related functional and mechanical qualities of athletes, for example their explosive power and smoothness of development of moment and impulse in vertical jumping.

Accordingly, such nonlinear timeseries analysis may be used to assess normal and abnormal physiologic states. In some embodiments, such analysis includes measures of time-domain variability but also frequently includes measures of disorder, such as sample entropy, approximate entropy, Shannon entropy, etc. In some embodiments, Fourier Transform and Wavelet Transform techniques are likewise used to examine power spectra and other second-order properties. Additionally, in some embodiments, high-order statistics including third- and higher-order cumulants, bispectra, and trispectra may be employed.

Figure 1B:
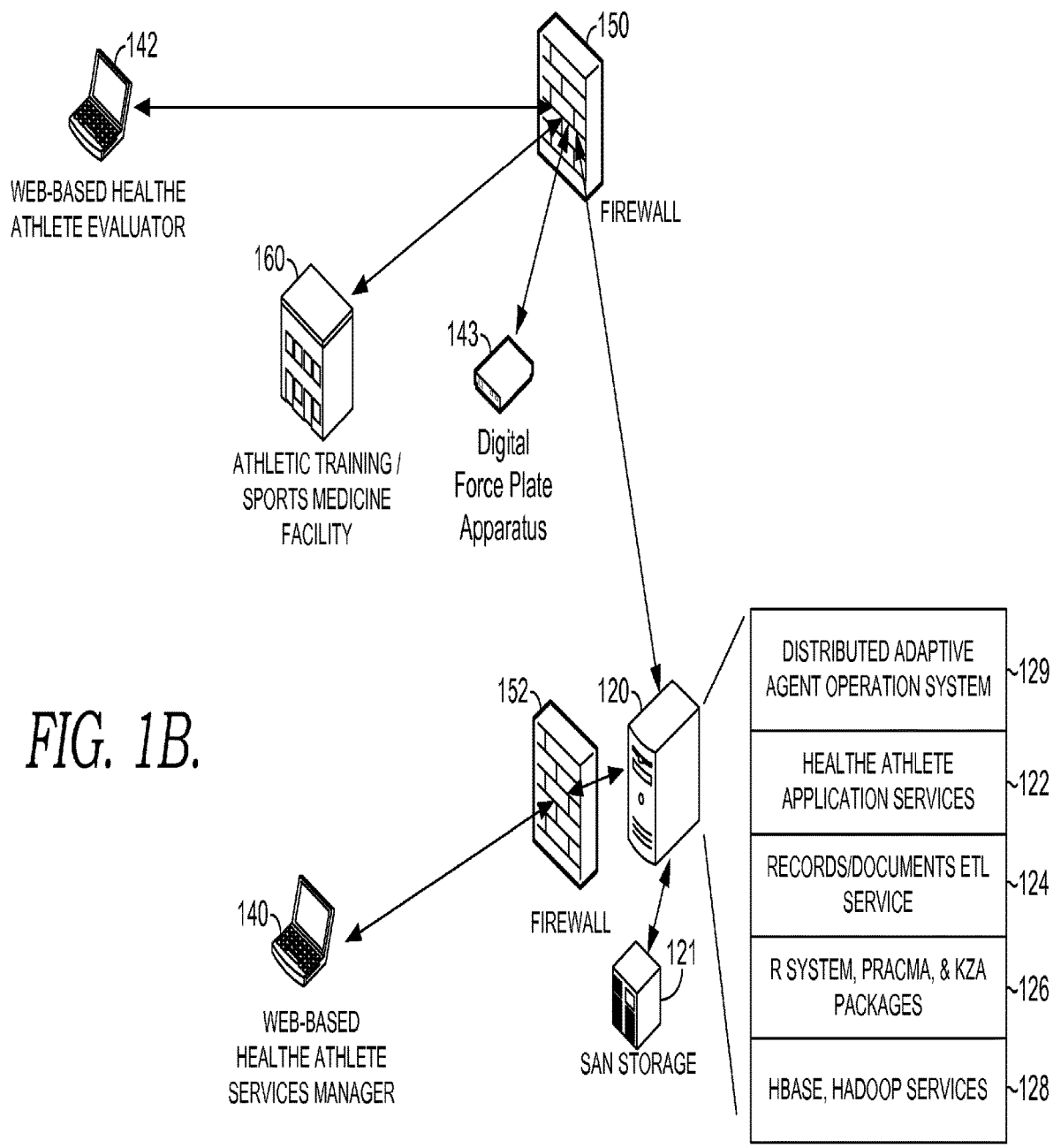

Turning now to FIGS. 1A and 1B, there is presented in 100 an example operating environment suitable for practicing embodiments of the invention. Example operating environment 100 includes a computerized system for compiling and running an embodiment of a decision support recommendation service. With reference to FIG. 1A, a first premise location 110 includes a private network behind firewall 150 communicatively coupled to Network 175. In example operating environment 100, client computing device 142, which can take the form of a mobile computing device, tablet, smart phone, front-end terminals in communication with back-end computing systems terminals, computer or laptop, communicates with Athletic Training or Sports Medicine Facility 160 and Bio-Mechanical Sensor 144. In embodiments, client device 142 includes an application (not shown) usable by an evaluator to monitor and evaluate the condition of a patient such as an athlete. In some embodiments, the application is web=-based, and in some embodiments, the web based application is Healthe® Athlete, developed by Cerner Corporation. Location 110 of example operating environment 100 also includes Bio-Mechanical Sensor 144, which includes one or more sensors operate to obtain time-series information from a patient or athlete. In some embodiments, sensor 144 includes a force-plate apparatus capable of capturing and providing jump-related information from a patient or athlete. Embodiments of sensor 144 are further described in connection to FIGS. 2A and 2B. Embodiments of Athletic Training or Sports Medicine Facility 160 (facility 160) include one or more computers or servers that run within a local or distributed private network.

Computer systems such as server 120 within premise 130 connect through firewall 152 to a private network and to public network 175 such as the internet to other premise 110 equipment and also to user computing device 140. In embodiments, computing device 140 may take the form of a mobile computing device, tablet, smart-phone, front-end terminals in communication with back-end computing systems terminals, laptop or other computing device. In some embodiments computing device 140 is capable of running an application (not shown), which can be web-based, that is usable by a manager to manage services provided by embodiments of the invention. In some embodiments device 140 is a usable by a user to monitor the condition of an athlete or patient, which in some scenarios may be the user.

Embodiments of computer software stack 121 run on a server such as 120 shown in FIGS. 1A and 1B. Embodiments of software stack 121 run as a distributed system on a virtualization layer within computers such as 160 and 120. Embodiments of software stack 121 include a distributed adaptive Agent operating system 129 that hosts a number of services such as 122, 124, 126, and 128. Embodiments of software programs 122, 124, 126 and 128 run as a local or distributed stack on a collection of personal computers and servers such as 142, 120, 160, and 140. Healthe Athlete Application services 122 provide services that facilitate the capturing, processing, storing, analyzing, and viewing of information obtained by bio-sensor 144 and related information, such as, for example, EMR information about a particular patient or athlete or set of patients or athletes, and metadata such as user preferences and performance metrics. Embodiments of Records/Documents ETL service 124 provide services that facilitate retrieving item sets, extracting database records, and cleaning the records' variable values. Software packages 126 perform statistical software operations, and in include statistical calculation packages such as, in one embodiment, the R system and R-system modules, packages such as Pracma for determining Entropy, and Kza for applying the Kolmogorov-Zurbenko Fourier Transform (KZFT). Embodiments of services 128 include Apache Hadoop and H base framework that provide a distributed file system.

FIG. 1B illustratively depicts another aspect of an example operating environment. Some of the components of FIG. 1B are described above with respect to FIG. 1A. Also shown in FIG. 1B is digital force plate apparatus 143, which is one example embodiment of biomechanical sensor 144. Force plate 143 is further described in connection to FIG. 2.

Also shown in FIG. 1B is data store 121, which in some embodiments includes patient data and information for multiple patients; variables associated with recommendations; recommendation knowledge base; recommendation rules; recommendations; recommendation update statistics; operational data store, which stores events; frequent itemsets (such as "X often happens with Y", for example) and itemsets index information; association rulebases, agent libraries, and other information, patient-derived data, healthcare provider information, for example. Although depicted as a single data store, may comprise more than one data store one or multiple locations, or in the cloud.

Figure 1C:
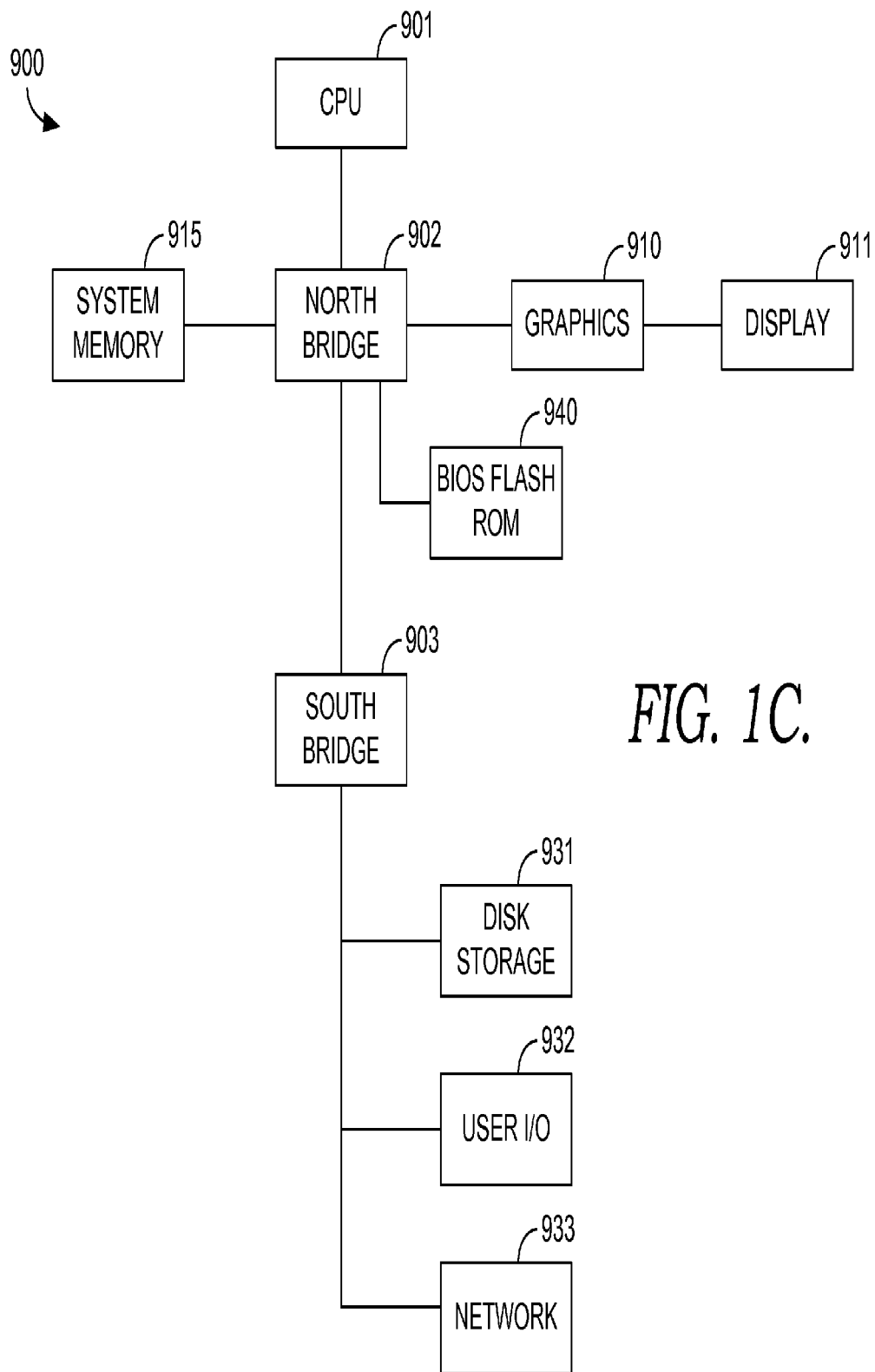

Turning now to FIG. 1C, there is shown one example of a computer system 900 that has software instructions for storage of data and programs in computer readable media. Computer system 900 is representative of a system architecture that could be used for computers such as 142, 140, 120 and 160. One or more CPU's such as 901 have internal memory for storage and couple to the North Bridge device 902, allowing CPU 901 to store instructions and data elements in system memory 915, or memory associated with graphics card 910 which is coupled to display 911. Bios flash ROM 940 couples to North Bridge device 902. South bridge device 903 connects to north Bridge device 902 allowing CPU 901 to store instructions and data elements in disk storage 931 such as a fixed disk or USB disk, or to make use of network 933 for remote storage. User IO device 932 such as a communication device, a mouse, a touch screen, a joystick, a touch stick, a trackball, or keyboard, couples to CPU through South Bridge 903 as well.

In some embodiments, computing system 900 is a computing system made up of one or more computing devices. In an embodiment, computing system 900 includes an adaptive multi-agent operating system, but it will be appreciated that computing system 900 may also take the form of an adaptive single agent system or a non-agent system. Computing system 900 may be a distributed computing system, a centralized computing system, a single computer such as a desktop or laptop computer or a networked computing system.

In some embodiments, computing system 900 is a multi-agent computer system with agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

Figure 2A:
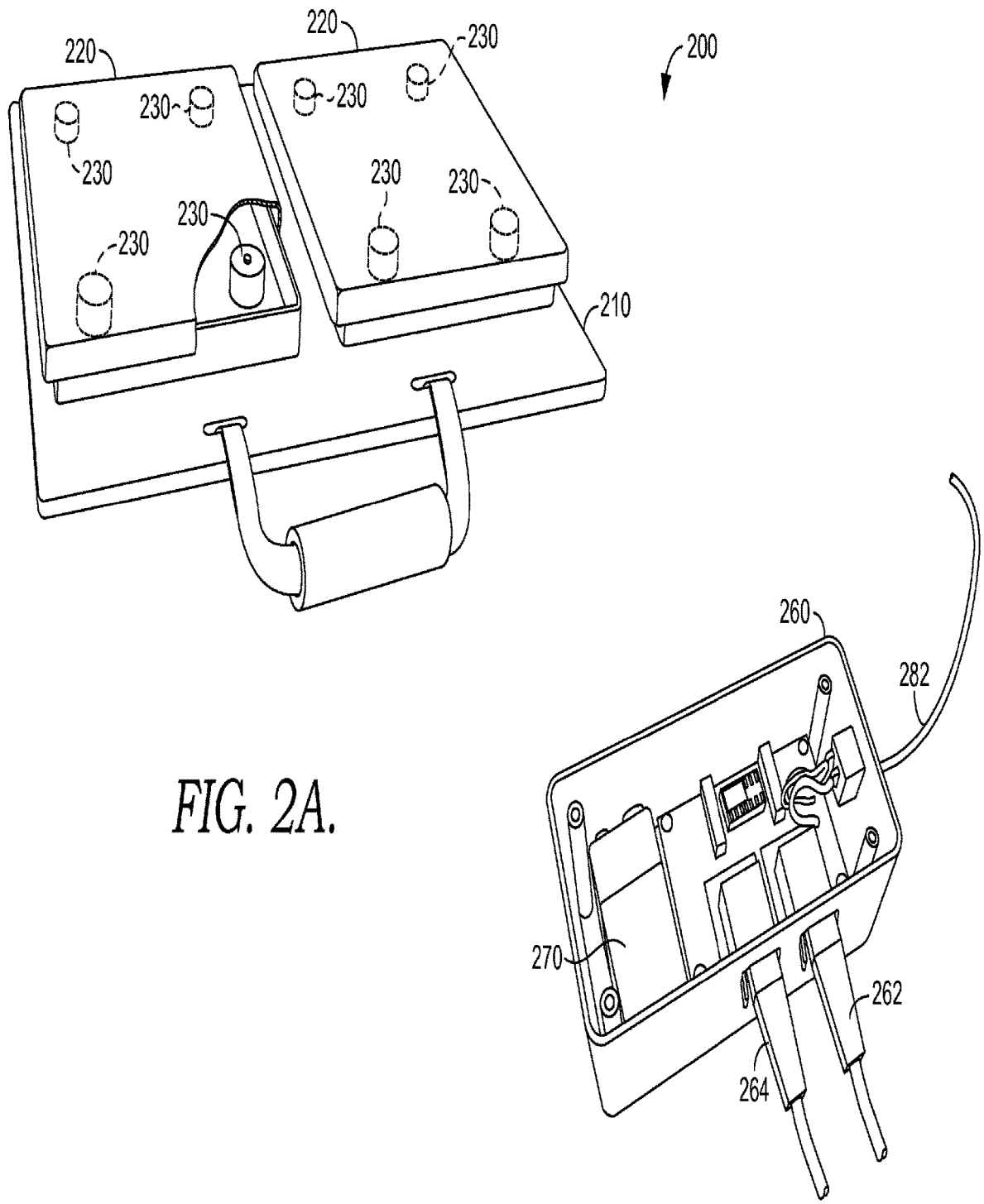
FIGS. 2A and 2B depict aspects of an embodiment for a biomechanical sensor capable of obtaining time-series information of movement.
Figure 2B:
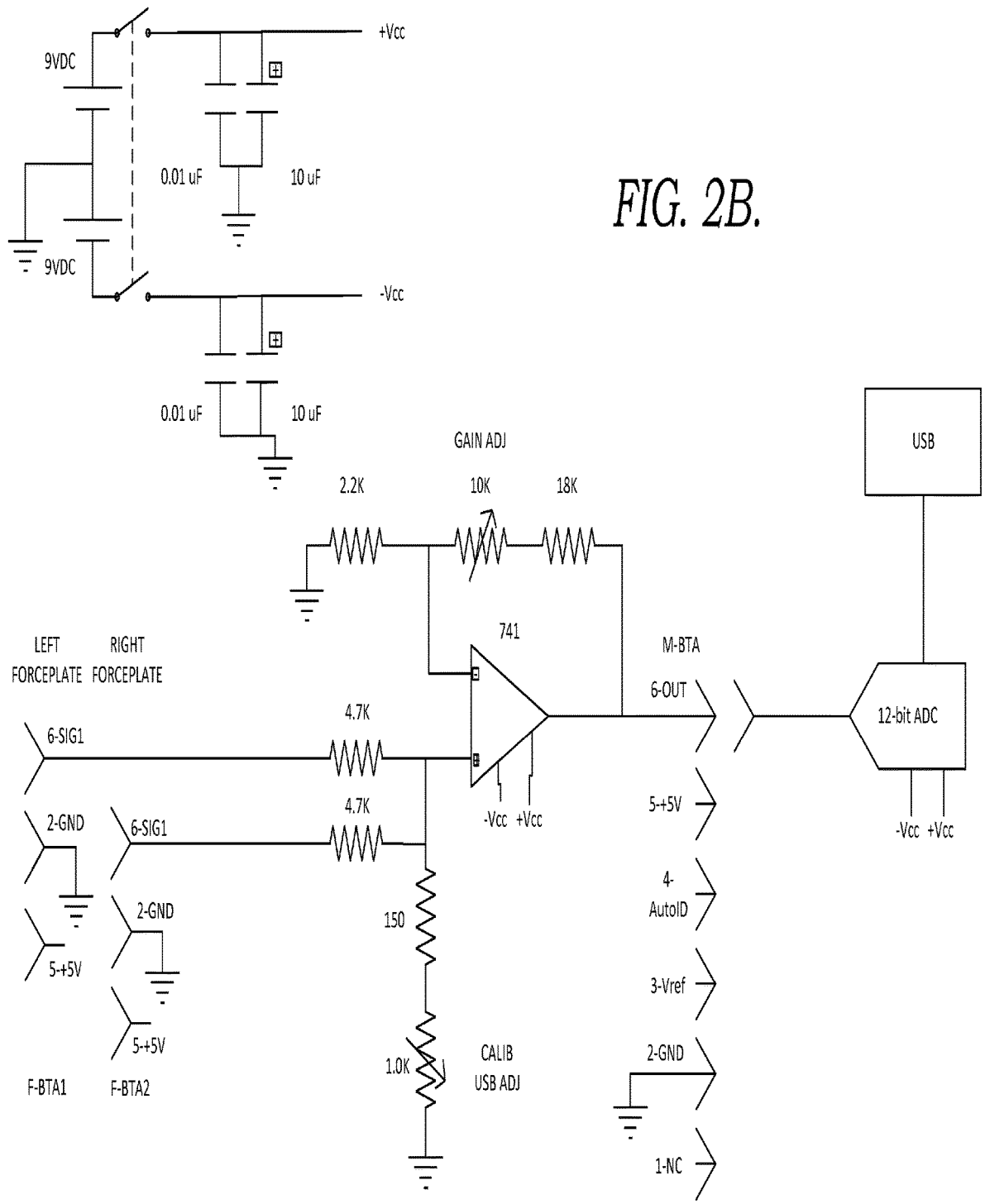

Turning now to FIGS. 2A and 2B, an example embodiment of biomechanical sensor 144 is shown. In this embodiment, a force plate apparatus, such as the apparatus 143 of FIG. 1B, is shown as force plate 200. By way of example, force plate 200 may be used to obtain jump-related time series information from a user, by having the user stand on surfaces 220, jump into the air, and land back down on surfaces 220. In the embodiment of FIG. 2A, a surface 220 is used by each foot. In this example embodiment, force plate 200 includes plate 210 which comprises a rigid or stiff material such as metal, rigid plastic, wood, or ceramic, for example. Force plate 200 further includes a surface 220 positioned on top of one or more load cells 230. Load cell 230 is operable to provide an electric measurement of the load (i.e. the weight) bearing down on the load cell. In the embodiment shown in FIGS. 2A and 2B, 8 load cells 230 are used, with one load cell positioned in each corner of surfaces 220. Force plate 220 is communicatively coupled to computing device 260, which samples and formats the values obtained from load cells 220. In one embodiment, computing device 260 includes a 9 volt battery 270, inputs 262 and 264, which are communicatively coupled to the left and right surfaces 220 and output 282, which is communicatively coupled through firewall 150 to network 175, facility 160, and computing device 142. In one embodiment, output 282 is a USB connection.

In some embodiments, force plate 200's sensors are connected to a computational system capable of acquiring signals from the force plate, digitizing them, storing them as a time series of longitudinal measurements, performing computations on the time series data, and displaying and storing the results of the computations. In some embodiments, force-plate 200's sensors provide time series measurements to computing device 260, which formats the information for use by computing devices 160, 140, 142, and/or 120. In some embodiments, force plate 200 incorporates computing device 260 inside its housing. In some embodiments, force plate wirelessly communicates information to a remotely located computing device 260, which in one embodiment takes the form of a mobile phone.

FIG. 2B shows an example embodiment of the electronic circuit employed in the example embodiment of FIG. 2A. Embodiments of force plate 200, or biomechanical sensor 144, can include multiple sensors, such as that depicted in FIG. 2A, which includes a left-foot and right-foot sensor. In some embodiments, it is important to obtain sufficient detail in the time series information obtained by biomechanical sensor 144, or force plate 200. Therefore in some embodiments the frequency response of force plate 200, or biomechanical sensor 144, is up to 400 HZ, and in some embodiments the fundamental resonant frequency is approximately 600 Hz. Examples of force plates suitable for use in some embodiments of the present invention include some of the force plate packages sold by the Bertec Corporation of Columbus, Ohio, such as the standard gait and impact package, standard high-impact package, and standard gait and posture package.

Figure 3A:
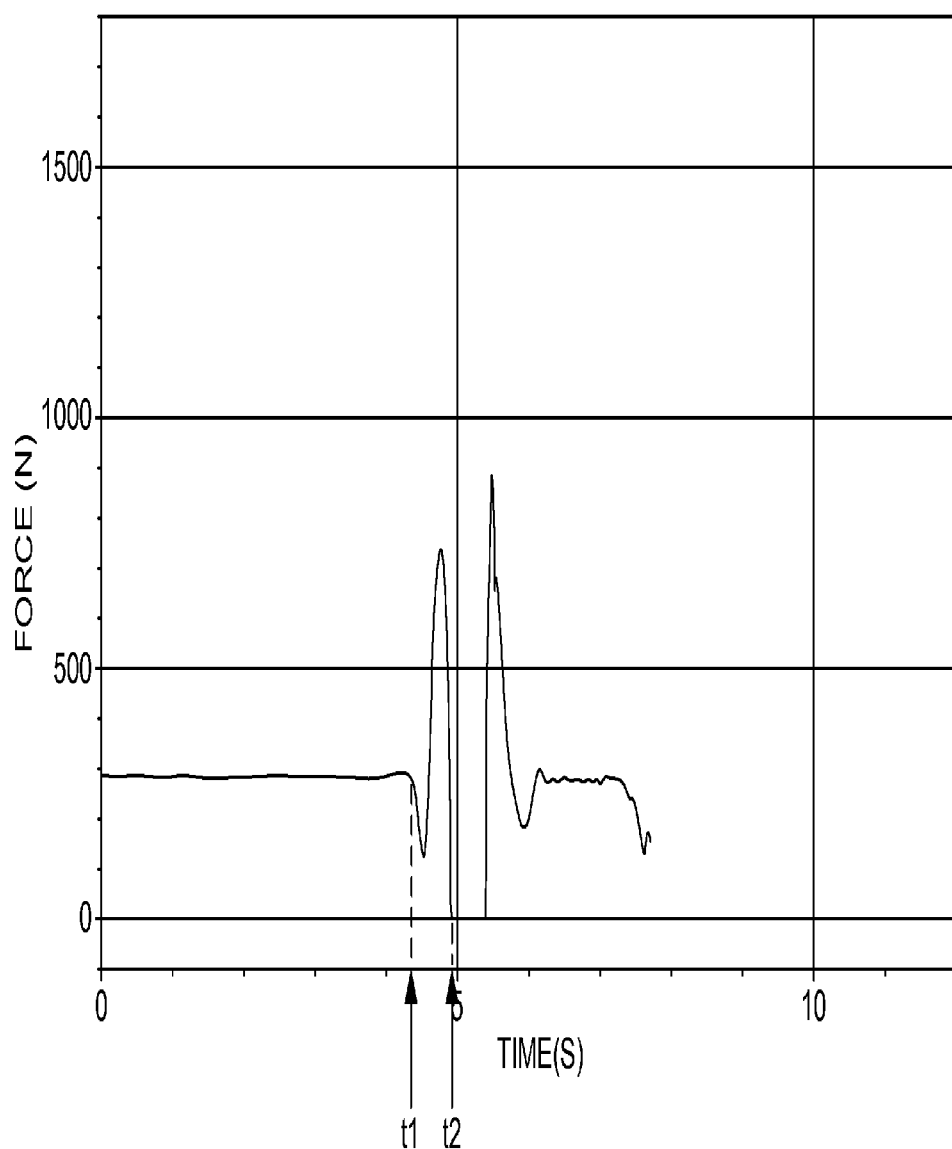
FIGS. 3A, 3B, and 3C depict example time-series information obtained from the biomechanical sensor of FIGS. 2A and 2B.
Figure 3B:
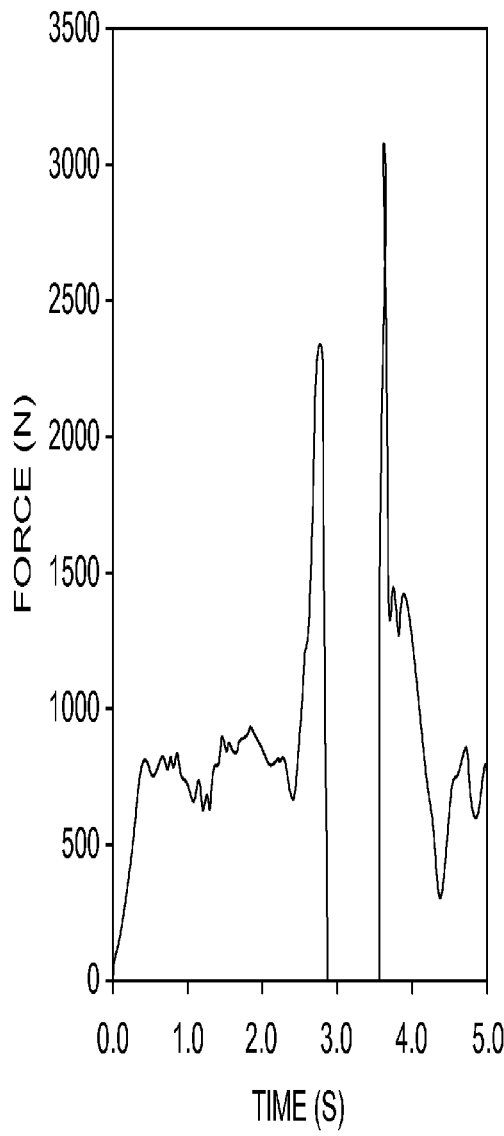
Figure 3C:
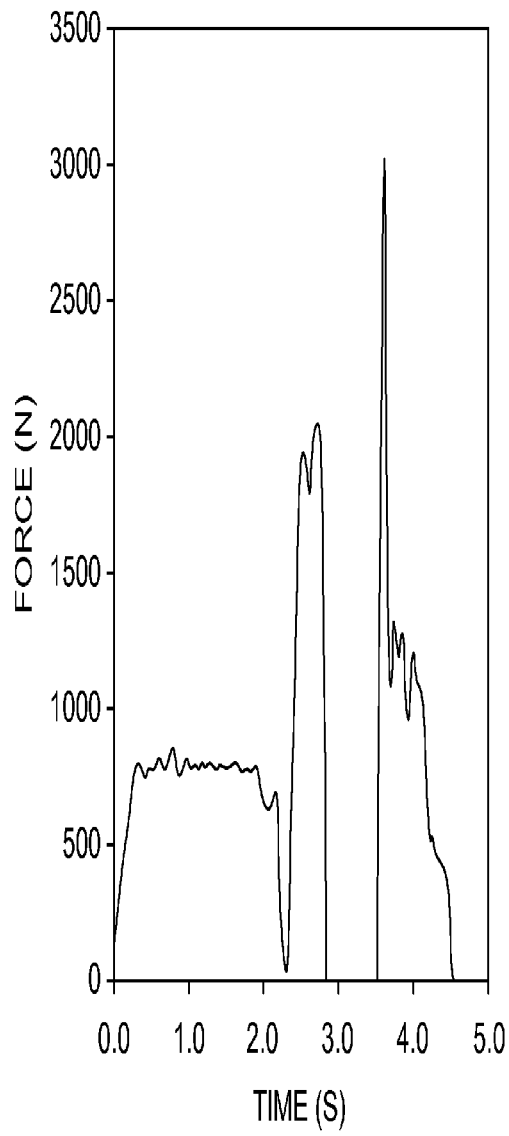

FIGS. 3A-3C illustrate example waveforms of time-series information obtained from a force plate such as force plate 200. As shown, the vertical dimension represents force (shown in N) and the horizontal dimension represents time. FIG. 3A and FIG. 3B shows a waveform from a squat jump and FIG. 3C depicts a waveform obtained from a counter-movement jump. Turning to FIG. 3A, a time interval is shown, bracketed by time t1 and time t2, which corresponds to the initial movement of the jumper immediately prior to leaving the ground. Some embodiments described in connection with the method of FIG. 5, process information obtained from this time interval.

Figures 4A, 4B:
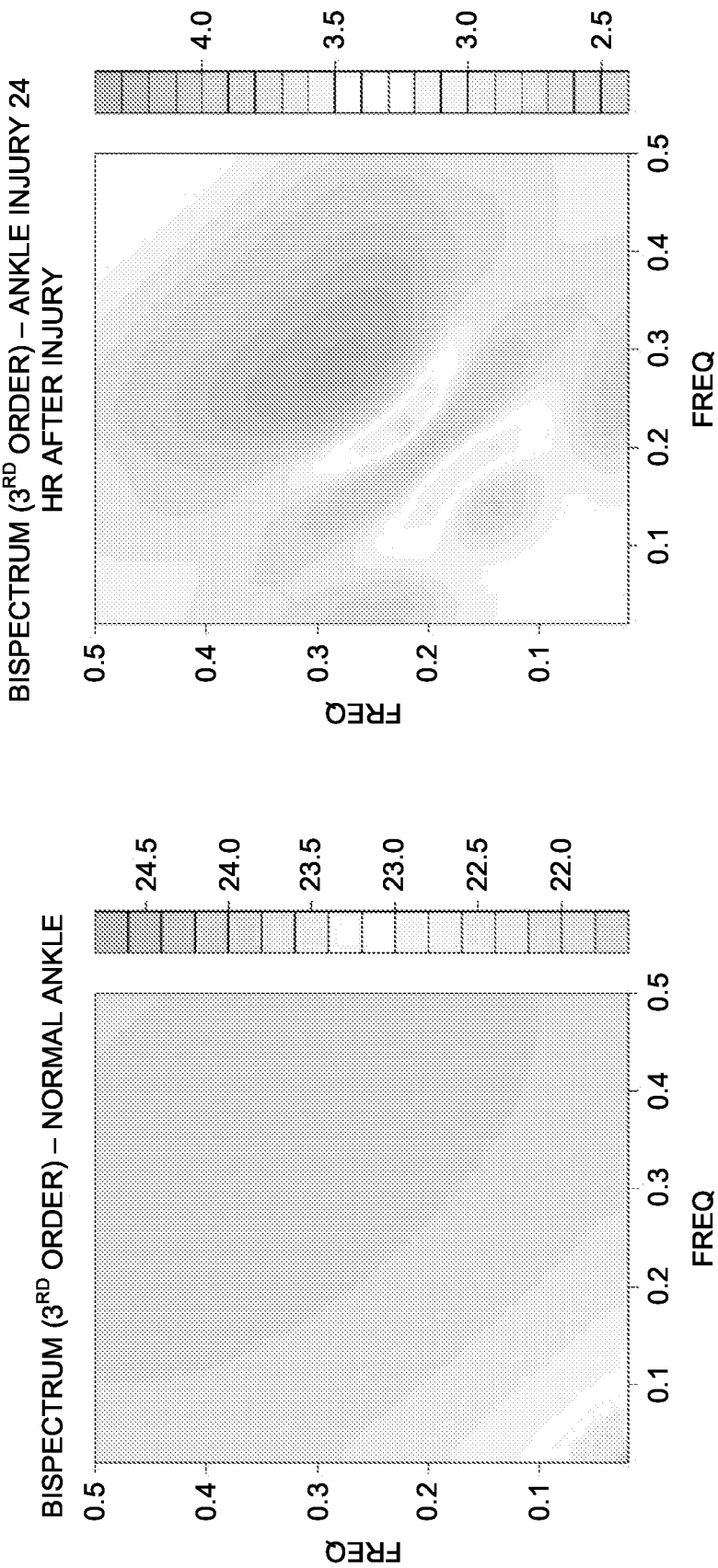
FIGS. 4A-4G depict a series of $3^{rd}$ order spectral analyses (bispectrum) of time series information obtained from an athlete over increasing periods times following an ankle injury.
Figure 4D:
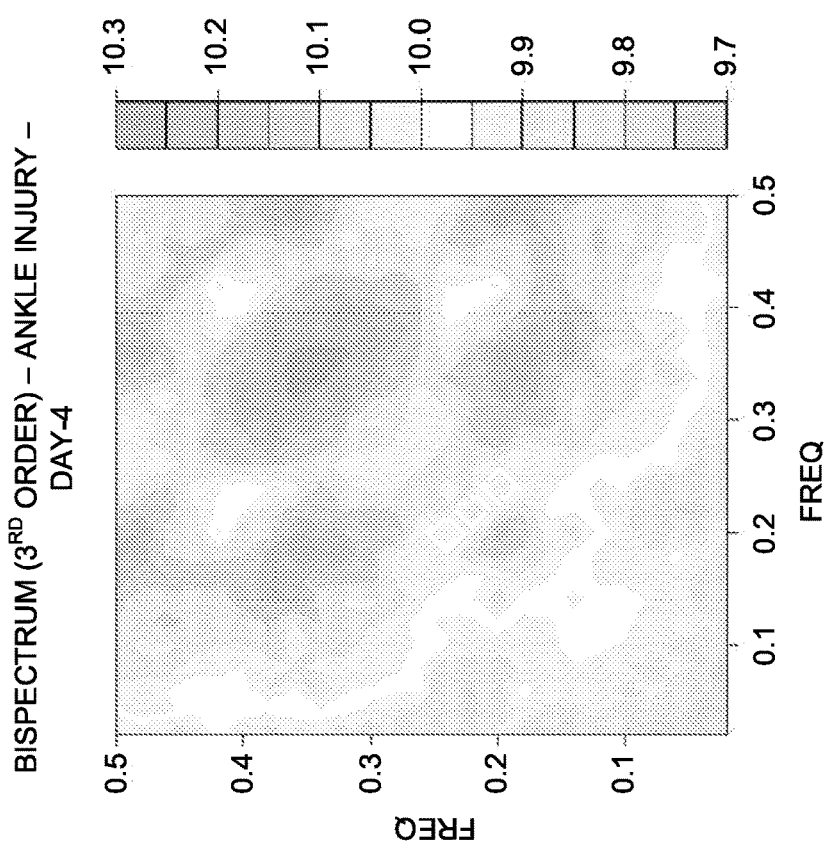
Figure 4C:
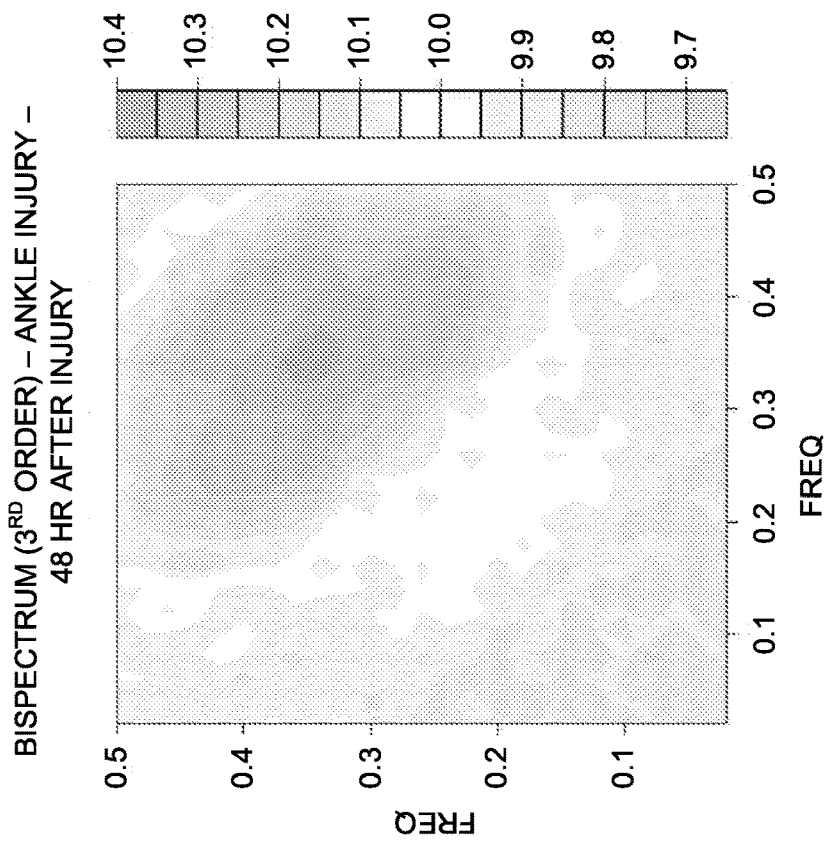
Figures 4E, 4F:
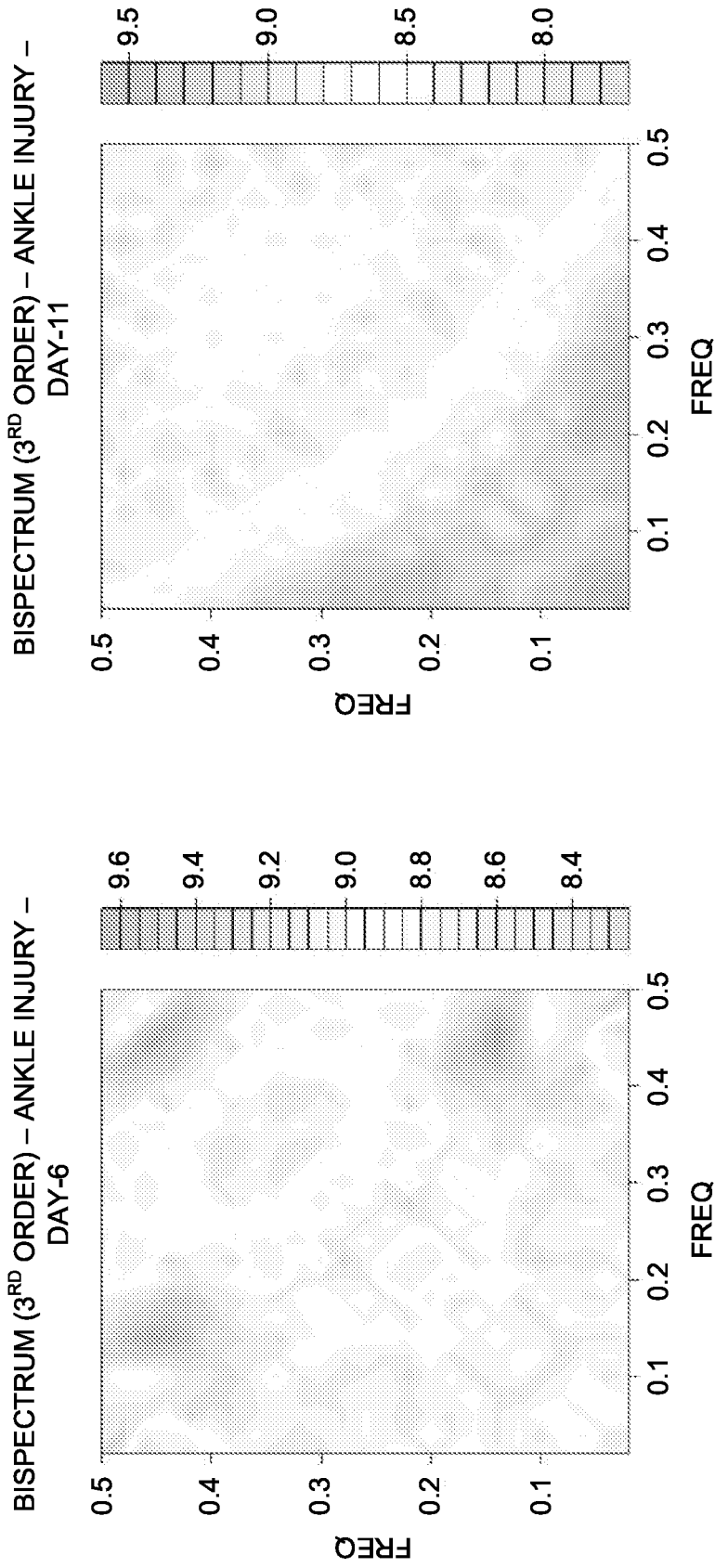
Figure 4G:
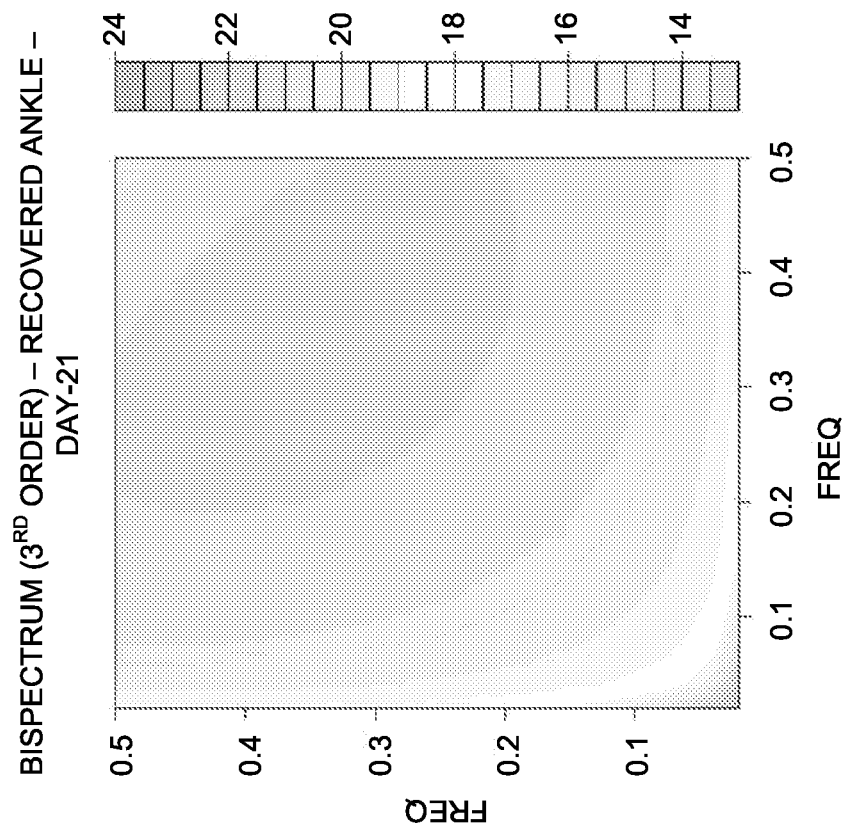

FIGS. 4A-4G depict embodiments of computed bispectra ($3^{rd}$ order) graphs resulting from time series information acquired from a squat jump of an individual. Such graphics may be used to assess an individual's fitness and recover status. FIG. 4A shows the result of an individual, which may be a patient or athlete, with a normal (healthy) ankle. FIGS. 4B through 4G show results of an individual having an ankle injury, with each figure showing an increasing time interval from the injury, starting at 24 hours after the injury (FIG. 4B) through 21 days after the injury (FIG. 4G). In this manner, health care provider or trainer can visually observe the fitness or recovery status of a patient or athlete.

Figure 5:
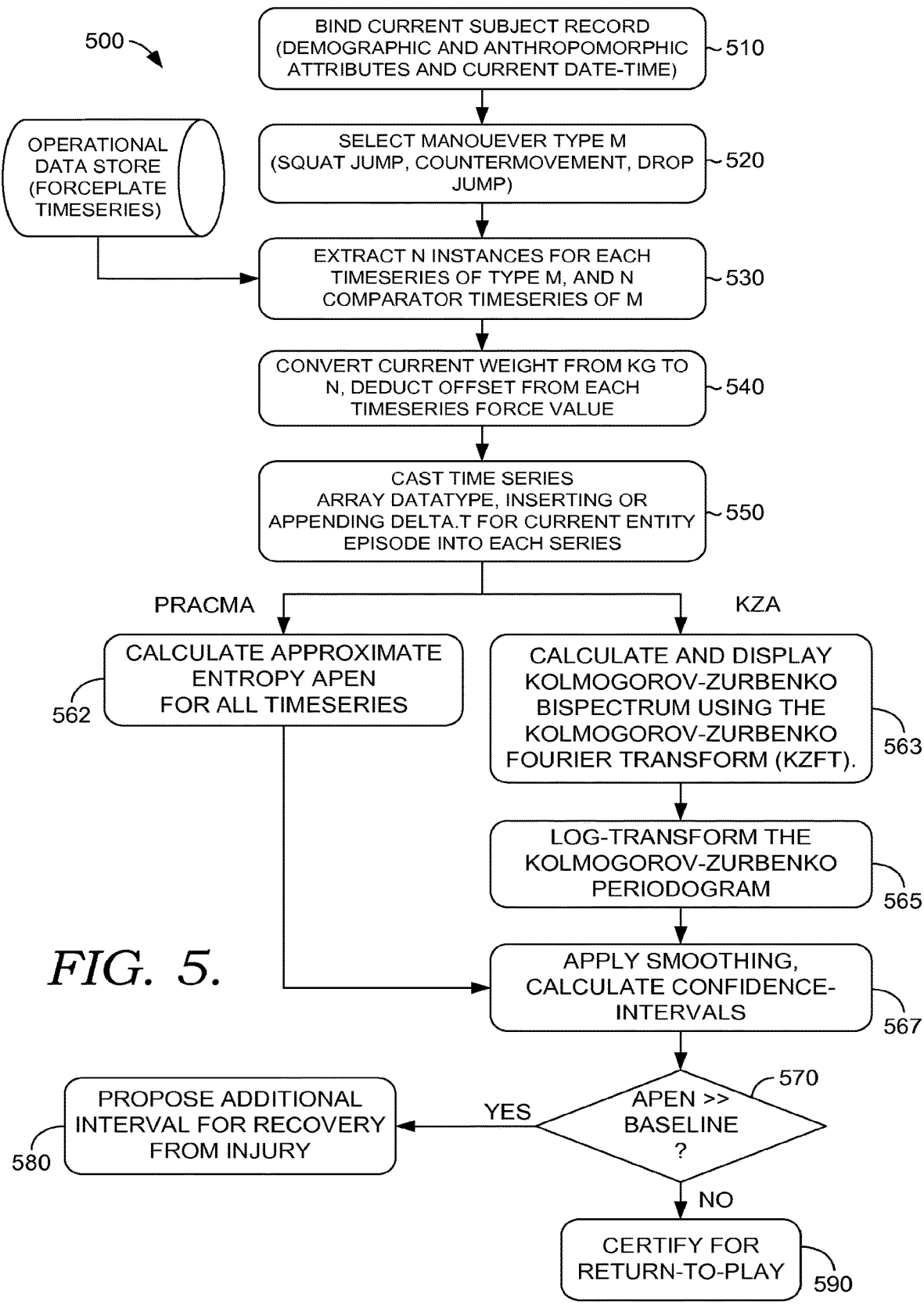
FIG. 5 depicts a flow diagram of an embodiment of a method for generating bispectra from a biomechanical sensor used to acquire force-vs.-time measurements associated with squat-jump and countermovement-jump maneuvers.

Turning now to FIG. 5, a flow diagram is provided, which depicts an embodiment of a method for generating bispectra from a biomechanical sensor used to acquire force-vs-time measurements associated with squat-jump and counter-movement-jump maneuvers. In this embodiment, functional capacity of athletes can be evaluated by means of a method, which uses brief testing involving maneuvers such as lifts and/or jumps. In this embodiment, a biomechanical sensor 144, such digital force plate 200, is used which is equipped with sensors including strain-gage, Hall Effect, piezoelectric or other force sensors, as are known to those practiced in the art. Digital force plate 200 may be affixed to the floor or other solid horizontal surface that is not susceptible to significant vibration or other movements emanating from any source other than an athlete standing or jumping on the force plate 200.

In some embodiments of the method depicted in FIG. 5, an athlete or patient may initiate a sequence of successive vertical jumping accelerations on force plate 200, such that at the end of the sequence of these maneuvers, at least one quantity representative of functional and mechanical capacity is obtained. In some embodiments, a display provides feedback for each jump, enabling an operator to determine if at least one quantity representative of functional and mechanical capacity has been obtained. In some embodiments, the capacities of the lower limbs may be calculated and displayed at the end of the test, for example in the form of the jump height, take-off velocity, maximum power, jump height percent of baseline, etc. In some embodiments, functional status, which may be reflected in the detailed fine-structure of the time series or the frequency-domain properties of spectra derived from the time series, may be determined and presented.

At a step 510, bind the record of the subject under test, including demographic attributes (age, gender, sport, position) and anthropometric attributes (height, current weight, current body mass index, percent body fat, knee valgus motion, knee flexion ROM angle, quadriceps-hamstring ratio, tibia length, foot inversion angle, foot eversion angle, plantar flexion angle, dorsiflexion angle, single-limb balance time, or similar attributes). At a step 520, select a plurality of baseline functional kinetic and kinematic variables including maximum jump height, take-off velocity, maximum power, or similar variables. At a step 530, extract, from Operational Data store, previous force plate time series records (if any exist) for the current test subject, as well as previous Approximate Entropy (ApEn) and bispectra if applicable, for comparison to new data associated with the current evaluation. At a step 540, for the current exam, acquire a minimum number of force plate time series, for squat jump and/or countermovement jump. In some embodiments, this minimum number is three. In some embodiments, the sampling rate should preferably be not less than 400 Hz and A-to-D conversion resolution should preferably be not less than 12 bits. In some embodiments, the signal may need to be de-noised. In some embodiments, morphologically identify the subset of the time series beginning at a stable interval before the jump begins and ending at the time when the force plate force reaches its nadir (zero, or near-zero) value and jump take-off occurs, and deduct the static force representing the subject's body weight in Newtons from each time series value. At a step 550, store the timeseries. In some embodiments, the time series is stored on data store 121, which in some embodiments comprises persistent machine-readable format on suitable electronic storage media. In some embodiments, cast time series array datatype, inserting or appending delta t for current entity episode into each time series.

At a step 562, determine the Approximate Entropy (ApEn) and at steps 563 and 565 determine the bispectra for each time series from Step 550. In some embodiments, bispectra is determined by applying the Kolmogorov-Zurbenko Fourier Transform. In some embodiments this is facilitated by the KZA package of software packages 126 of FIG. 1A. Likewise, in some embodiments Approximate Entropy is determined using the Pracma package included in software packages 126. At a step 567, apply smoothing and determine confidence intervals by calculating the statistical significance p-value. At a step 570, compare the ApEn of the current time series to the ApEn of selected baseline jump time series. At a step 580 propose additional interval for recovery from injury, based on step 570. Alternatively, at a step 590, certify individual for return to play. In some embodiments of steps 570-590, display the bispectra and the ApEn and the significance p-value on a computer graphical user interface. In some embodiments of these steps, simultaneously display other interpretive annotations or alerts if applicable. In some embodiments of these steps, request that the operator (trainer, kinesiologist, physical therapist, other user) decide whether or not to record a decision regarding RTP or other disposition of the athlete, based on the findings observed in the current testing. Store the annotation or decision if applicable) on electronic storage media, with the user's identification and date-time stamp of the disposition decision.

Example 1

The following example embodiment implements a force-plate bispectrum subsystem that was reduced to practice using a server cluster running the Linux operating system, the open-source statistical software package R, and the R packages kza and pracma. Cerner CareAware iBus® was used to capture time series from a Hall Effect force plate with 600 Hz sampling rate and 12-bit ADC. Force plate time series, ApEn, and bispectrum, data were stored in Cerner Healthe Athlete® information system, which was also used to store player demographics and anthropometric variable information.

After granting informed consent, volunteer amateur basketball players were studied using a protocol that involved standard squat jumps on both a standard strain gauge laboratory force plate and a portable Hall Effect sensor force plate. To emulate conditions of play and patterns of neuromuscular recruitment and fatigue, the protocol involved 10 warm-up jumps at approximately 50% of the 1RM maximal force and jump-height, with 1 minute between each warm-up jump. Following the warm-up segment, consecutive measured squat jumps were maximal (at 1-repetition-maximum 1RM load) and were separated by an interval of 2 minutes, to allow the subject to rest and prepare for the next jump. Subsequent to the initial baseline evaluations, several subjects experienced injuries to the lower extremity (ankle, knee, hip). During the days of the recovery from the injuries, subjects who were able to perform squat jumps attempted the squat jump manoeuver on the force plate apparatus, similar to force plate 200, and time series were acquired. Results of the method described in connection to FIG. 5 reveal that the Approximate Entropy (ApEn) was acutely higher than baseline during the early phases of the recovery process. Similarly, the bispectra exhibited abnormal, diffuse spectral peaks which abated as recovery proceeded and strength and function returned to the injured extremity.

In some instances, causes of the abnormal bispectra may be difficult to ascertain, and may include abnormal stiffness or stiction of the joints or joint surfaces; compensatory movements to avoid applying undue forces or moments about the injured structures; abnormal rate and extent of neuromuscular recruitment of muscle fibers to develop torque at the joints involved in jumping; psychological activity inhibiting smooth and confident voluntary muscular activity; and other factors. Regardless what the multifactorial nature of the cause(s) may be, the statistically significant divergence of ApEn and bispectral features from baseline values do comprise a relatively sensitive and specific means of detecting and assessing injury to the lower extremity, and a valuable means for monitoring recovery progress toward normal baseline functioning.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the claims.

Some embodiments of the present invention include methods and computer readable media having computer-executable instructions embodied thereon for performing a method of determining estimated jump height, take-off velocity, and power, the method comprising steps of: obtaining dynamic and kinematic data from the system; obtaining input forces and maneuver types for the system; computing a modified acceleration using at least the kinematic data; and performing entropy and spectral analysis using the time series to determine simulated kinematic data for the system.

Some embodiments further include wherein the input force comprises a ground reaction force; some embodiments further include wherein the input force comprises digital force plate measurement of force; and some embodiments further include that manoeuver types comprise one or more of the following: squat jump, countermovement jump, and drop jump.

In some embodiments, input forces comprise one or more of the following: the person's body weight, and additional vertical resistance force or free-weights. In some embodiments, dynamic and kinematic data are acquired by means of a force plate equipped with sensors capable of measuring forces preferably in the range −1,000 N to +10,000 N with accuracy and linearity of at least 0.2% full-scale and natural frequency not less than 400 Hz.

Some embodiments include providing original kinetic response data from a physiologic structure, both before and after injury; computing a plurality of bispectra from the said force plate data; and identifying injury-induced non-linearity from a difference between the plurality of bispectra from the original structural response data and the plurality of bispectra from the pre-injury data.

Moreover, some embodiments include providing time series structural response data from a physiologic structure; estimating a generalized correlation function to calculate a confidence interval or a p-level or both; estimating an approximate entropy indicating injury-associated nonlinearity in the structure when the collection of outputs of the generalized correlation function applied to the structural response data is outside of the confidence interval or is statistically significant at a selected p-level. Some embodiments further include performing a comparison of said collections of outputs of approximate entropy and related structural response data using non-parametric statistical tests, such as the two-sample Mann-Whitney-Wilcoxon rank-sum test.

The invention claimed is:

1. A computing device for determining residual abnormalities from an injury to a person, the computing device comprising:
   one or more biomechanical sensors configured to detect movement related time series information;
   one or more processors;
   memory, coupled with the one or more processors, having instructions stored thereon which are configured to, when executed by the one or more processors, cause the one or more processors to:
   receive, from the one or more biomechanical sensors, motion information corresponding to post-injury movements of the person;
   generate, based on the motion information, a time series of the post-injury movements, wherein the time series reflects an amount of force applied over time during the post-injury movements;
   perform an entropy analysis using the time series of the post-injury movements to calculate an approximate entropy;
   receive a selection of one or more baseline approximate entropies;
   determine the residual abnormalities of the injury to the person based on differences between the approximate entropy and pre-injury data, and evaluate time-series based differences between the approximate entropy and the one or more baseline approximate entropies of the person; and
   present via a display, based on the residual abnormalities and the time-series based differences, at least one of an additional recovery time proposal or a return to play certification.

2. The computing device of claim 1, the instructions further configured to cause the one or more processors to:
   generate simulated kinematic information based at least in part on the approximate entropy, wherein to determine the residual abnormalities of the injury to the person is further based on the simulated kinematic information.

3. The computing device of claim 2, wherein the simulated kinematic information is used to determine a time interval representing a time until the person is able to resume athletic activity.

4. The computing device of claim 2, wherein the simulated kinematic information is used to prescribe treatment for the person.

5. The computing device of claim 1, wherein the one or more biomechanical sensors comprises one or more load cells.

6. The computing device of claim 1, wherein the motion information includes at least one of jump-height, take off velocity, and power.

7. The computing device of claim 1, wherein the motion information comprises dynamic or kinematic data.

8. The computing device of claim 1, the instructions further configured to cause the one or more processors to:
   determine time series structural response data of a physiologic structure of the person based on the motion information;
   based on the time series structural response data, determine at least one of a confidence interval and a p-level; and
   determine an entropy value indicating injury-associated nonlinearity in the physiologic structure of the person when a collection of outputs of a generalized correlation function applied to the time series structural response data is outside of the confidence interval at a selected p-level;
   wherein determining at least one of the confidence interval and the p-level comprises estimating the generalized correlation function.

9. The computing device of claim 8, the instructions further configured to cause the one or more processors to:
   perform a comparison of the collection of outputs and related structural response data using a two-sample Mann-Whitney-Wilcoxon rank-sum test or a non-parametric statistical tests.

10. One or more computer-readable storage device having computer-executable instructions embodied thereon which are configured to, when executed by one or more processors, cause the one or more processors to:

receive, from one or more biomechanical sensors, motion information corresponding to post-injury movements of a person;

generate, based on the motion information, a time series of the post-injury movements, wherein the time series reflects an amount of force applied over time during the post-injury movements;

perform an entropy analysis using the time series of the post-injury movements to calculate an approximate entropy;

receive a selection of one or more baseline approximate entropies;

determine residual abnormalities of an injury to the person based on differences between the approximate entropy and pre-injury data and evaluate time-series based differences between the approximate entropy and the one or more baseline approximate entropies; and present via a display, based on the determination of the residual abnormalities and the evaluation of the time-series based differences, at least one of an additional recovery time proposal or a return to play certification.

11. The one or more computer-readable storage device of claim 10, the instructions further configured to cause the one or more processors to:

generate simulated kinematic information based at least in part on the approximate entropy, wherein the motion information includes at least one of jump-height, take-off velocity, and power.

12. The one or more computer-readable storage device of claim 10, wherein the motion information comprises dynamic or kinematic data.

13. The one or more computer-readable storage device of claim 12, wherein the motion information further comprises input force and maneuver types.

14. The one or more computer-readable storage device of claim 13, wherein the input force comprises a ground reaction force.

15. The one or more computer-readable storage device of claim 13, wherein the input force is received from a digital force plate.

16. The one or more computer-readable storage device of claim 12, wherein the dynamic or kinematic data are received from a force plate comprising sensors capable of measuring forces in a range substantially comprising $-1,000$ N to $+10,000$ N with accuracy and linearity of at least 0.2% full-scale and natural frequency not less than 400 Hz.

17. The one or more computer-readable storage device of claim 13, wherein the input force comprises a body weight of the person or the body weight of the person and at least one of additional vertical resistance force or free-weights.

18. The one or more computer-readable storage device of claim 10, the instructions further configured to cause the one or more processors to:

determine time series structural response data of a physiologic structure of the person based on the motion information;

based on the time series structural response data, determine at least one of a confidence interval and a p-level; and determine an entropy value indicating injury-associated nonlinearity in the physiologic structure of the person when a collection of outputs of a generalized correlation function applied to the time series structural response data is outside of the confidence interval at a selected p-level;

wherein determining at least one of the confidence interval and the p-level comprises estimating the generalized correlation function.

19. The one or more computer-readable storage device of claim 18, the instructions further configured to cause the one or more processors to:

perform a comparison of the collection of outputs and related structural response data using a two-sample Mann-Whitney-Wilcoxon rank-sum test or a non-parametric statistical tests.

20. A system for determining residual abnormalities from an injury to a person, the system comprising:

one or more biomechanical sensors configured to detect movement related time series information;

one or more processors;

memory, coupled with the one or more processors, having instructions stored thereon which are configured to, when executed by the one or more processors, cause the one or more processors to:

receive, from the one or more biomechanical sensors, motion information corresponding to post: injury movements of the person;

generate, based on the motion information, a time series of the post-injury movements, wherein the time series reflects an amount of force applied over time during the post-injury movements;

perform an entropy analysis using the time series of the post-injury movements to calculate an approximate entropy;

receive a selection of one or more baseline approximate entropies;

determine the residual abnormalities of the injury to the person based on differences between the approximate entropy and pre-injury data and evaluate time-series based differences between the approximate entropy and the one or more baseline approximate entropies of the person; and present via a display, based on the residual abnormalities and the time-series based differences, at least one of an additional recovery time proposal or a return to play certification.

* * * * *

UNITED STATES PATENT AND TRADEMARK OFFICE
CERTIFICATE OF CORRECTION

| | | |
|---|---|---|
| PATENT NO. | : 10,916,345 B1 | Page 1 of 1 |
| APPLICATION NO. | : 15/888955 | |
| DATED | : February 9, 2021 | |
| INVENTOR(S) | : Douglas S. McNair | |

It is certified that error appears in the above-identified patent and that said Letters Patent is hereby corrected as shown below:

In the Drawings

Figure 5, Sheet 12 of 12, Reference Numeral 520: Please remove "MANOUEVER" and replace with --MANEUVER--.

In the Specification

Column 03, Line 34: Please remove "(RIP)" and replace with --(RTP)--.

Column 06, Line 20: Please remove "H base" and replace with --Hbase--.

In the Claims

Column 12, Line 18: Please remove "return to play" and replace with --return-to-play--.

Column 12, Line 37: Please remove "take off" and replace with --take-off--.

Column 13, Line 21: Please remove "return to play" and replace with --return-to-play--.

Column 13, Line 50: Please remove "person or" and replace with --person, or--.

Column 14, Line 32: Please remove "post: injury" and replace with --post-injury--.

Column 14, Line 51: Please remove "return to play" and replace with --return-to-play--.

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*